(12) United States Patent
Levi (10) Patent No.: US 11,998,446 B2
(45) Date of Patent: *Jun. 4, 2024

(54) GRIPPING AND PUSHING DEVICE FOR MEDICAL INSTRUMENT

(71) Applicant: Edwards Lifesciences Corporation, Irvine, CA (US)

(72) Inventor: Tamir S. Levi, Zikhron Yaakov (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 141 days.

This patent is subject to a terminal disclaimer.

(21) Appl. No.: 17/587,843

(22) Filed: Jan. 28, 2022

(65) Prior Publication Data

US 2022/0151778 A1 May 19, 2022

Related U.S. Application Data

(63) Continuation of application No. 16/222,992, filed on Dec. 17, 2018, now Pat. No. 11,234,814, which is a
(Continued)

(51) Int. Cl.
*A61F 2/24* (2006.01)
*A61F 2/95* (2013.01)
(Continued)

(52) U.S. Cl.
CPC .............. *A61F 2/2427* (2013.01); *A61F 2/95* (2013.01); *A61M 25/0113* (2013.01);
(Continued)

(58) Field of Classification Search
CPC ..... A61F 2/2427; A61F 2/95; A61M 25/0113; A61M 25/09041
See application file for complete search history.

(56) References Cited

U.S. PATENT DOCUMENTS

| 519,297 A | 5/1894 | Bauer |
|---|---|---|
| 2,009,825 A | 7/1935 | Wappler |

(Continued)

FOREIGN PATENT DOCUMENTS

| DE | 19532846 A1 | 3/1997 |
|---|---|---|
| DE | 19907646 A1 | 8/2000 |

(Continued)

OTHER PUBLICATIONS

International Search Report for PCT/US2016/046545 dated Nov. 17, 2016.

*Primary Examiner* — Phong Son H Dang
(74) *Attorney, Agent, or Firm* — Klarquist Sparkman, LLP; Joel B. German (57) ABSTRACT

In one representative embodiment, a gripping and pushing device for a medical instrument comprises an elongated main body defining a lumen. The elongated main body comprises one or more deflectable portions that can be pressed radially inwardly toward a shaft of the medical instrument extending through the lumen. One or more elastomeric gripping layers can be secured to the inner surface of a respective deflectable portion at axially spaced apart attachment locations. The one or more gripping layers are axially deformable relative to the one or more deflectable portions between the attachment locations when manual pressure is applied to the one or more deflectable portions to press the one or more gripping layers against the shaft and move the shaft longitudinally into a patient's body.

24 Claims, 3 Drawing Sheets

Related U.S. Application Data continuation of application No. 15/232,722, filed on Aug. 9, 2016, now Pat. No. 10,179,046.

(60) Provisional application No. 62/205,567, filed on Aug. 14, 2015.

(51) Int. Cl.
*A61M 25/01* (2006.01)
*A61B 17/00* (2006.01)
*A61M 25/09* (2006.01)

(52) U.S. Cl.
CPC . *A61M 25/013* (2013.01); *A61B 2017/00469* (2013.01); *A61M 25/09041* (2013.01); *A61M 2025/09116* (2013.01)

(56) References Cited

U.S. PATENT DOCUMENTS

| | | | |
|---|---|---|---|
| 4,035,849 A | 7/1977 | Angell et al. | |
| 4,592,340 A | 6/1986 | Boyles | |
| 4,726,369 A * | 2/1988 | Mar | A61M 25/09041 606/1 |
| 4,858,810 A * | 8/1989 | Intlekofer | A61B 17/3403 24/115 M |
| 4,955,895 A | 9/1990 | Sugiyama et al. | |
| 4,994,077 A | 2/1991 | Dobben | |
| 5,059,177 A | 10/1991 | Towne et al. | |
| 5,137,517 A | 8/1992 | Loney et al. | |
| 5,176,698 A | 1/1993 | Burns et al. | |
| 5,192,297 A | 3/1993 | Hull | |
| 5,266,073 A | 11/1993 | Wall | |
| 5,325,746 A * | 7/1994 | Anderson | B25B 25/00 606/1 |
| 5,325,845 A | 7/1994 | Adair | |
| 5,325,868 A * | 7/1994 | Kimmelstiel | A61B 17/22 600/585 |
| 5,358,496 A | 10/1994 | Ortiz et al. | |
| 5,392,778 A * | 2/1995 | Horzewski | A61M 25/09041 600/434 |
| 5,411,552 A | 5/1995 | Andersen et al. | |
| 5,423,331 A | 6/1995 | Wysham | |
| 5,554,185 A | 9/1996 | Block et al. | |
| 5,591,195 A | 1/1997 | Taheri et al. | |
| 5,599,305 A | 2/1997 | Hermann et al. | |
| 5,632,760 A | 5/1997 | Sheiban et al. | |
| 5,634,475 A * | 6/1997 | Wolvek | A61M 25/09041 600/585 |
| 5,639,274 A | 6/1997 | Fischell et al. | |
| 5,728,068 A | 3/1998 | Leone et al. | |
| 5,749,890 A | 5/1998 | Shaknovich | |
| 5,782,809 A | 7/1998 | Umeno et al. | |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,961,536 A | 10/1999 | Mickley et al. | |
| 5,968,068 A | 10/1999 | Dehdashtian et al. | |
| 6,019,777 A | 2/2000 | Mackenzie | |
| 6,027,510 A | 2/2000 | Alt | |
| 6,030,349 A * | 2/2000 | Wilson | A61M 25/09041 600/585 |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,276,084 B2 | 10/2007 | Yang et al. | |
| 7,318,278 B2 | 1/2008 | Zhang et al. | |
| 7,320,702 B2 | 1/2008 | Hammersmark et al. | |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,699,809 B2 * | 4/2010 | Urmey | A61M 25/0606 607/116 |
| 7,780,723 B2 | 8/2010 | Taylor | |
| 7,785,366 B2 | 8/2010 | Maurer et al. | |
| 7,959,661 B2 | 6/2011 | Hijlkema et al. | |
| 7,972,282 B2 | 7/2011 | Clark et al. | |
| 8,025,629 B2 * | 9/2011 | Shelton | A61M 25/09041 81/487 |
| 8,029,556 B2 | 10/2011 | Rowe | |
| 8,167,932 B2 | 5/2012 | Bourang et al. | |
| RE43,882 E | 12/2012 | Hopkins et al. | |
| 8,449,606 B2 | 5/2013 | Eliasen et al. | |
| 8,475,523 B2 | 7/2013 | Duffy | |
| 8,568,472 B2 | 10/2013 | Marchand et al. | |
| 9,061,119 B2 | 6/2015 | Le et al. | |
| 9,119,716 B2 | 9/2015 | Lee et al. | |
| 9,700,703 B2 * | 7/2017 | Cude | A61M 25/09041 |
| 9,795,477 B2 | 10/2017 | Tran et al. | |
| D813,383 S * | 3/2018 | Kearns | D24/127 |
| 10,349,958 B2 * | 7/2019 | Schaeffer | A61B 17/22012 |
| 10,639,451 B2 * | 5/2020 | Kearns | A61M 25/002 |
| 2001/0002445 A1 | 5/2001 | Vesely | |
| 2001/0007082 A1 | 7/2001 | Dusbabek et al. | |
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2003/0226421 A1 * | 12/2003 | Livingston | B62K 21/26 74/551.1 |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0070820 A1 * | 3/2005 | Boutillette | A61M 25/09041 604/528 |
| 2005/0080474 A1 | 4/2005 | Andreas et al. | |
| 2005/0096688 A1 | 5/2005 | Slazas et al. | |
| 2005/0096736 A1 | 5/2005 | Osse et al. | |
| 2005/0137689 A1 | 6/2005 | Salahieh et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Zadno-Azizi | |

(56) References Cited

U.S. PATENT DOCUMENTS

| | | |
|---|---|---|
| 2005/0277946 A1* | 12/2005 | Greenhalgh ....... A61B 17/3498 606/108 |
| 2006/0025857 A1 | 2/2006 | Bergheim et al. |
| 2006/0058738 A1* | 3/2006 | Ponzi .................... A61M 25/02 604/180 |
| 2006/0217687 A1 | 9/2006 | Bakos et al. |
| 2006/0282150 A1 | 12/2006 | Olson et al. |
| 2007/0005131 A1 | 1/2007 | Taylor |
| 2007/0066963 A1* | 3/2007 | Tanghoj ............ A61M 25/0017 604/523 |
| 2007/0073389 A1 | 3/2007 | Bolduc et al. |
| 2007/0088431 A1 | 4/2007 | Bourang et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0051630 A1* | 2/2008 | Levey ...................... A61B 1/12 600/114 |
| 2008/0065011 A1 | 3/2008 | Marchand et al. |
| 2008/0097362 A1* | 4/2008 | Mosler .................. A61M 25/02 604/349 |
| 2008/0125853 A1 | 5/2008 | Bailey et al. |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0076417 A1 | 3/2009 | Jones |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2010/0286664 A1 | 11/2010 | Haslinger |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2011/0306900 A1 | 12/2011 | Whittaker et al. |
| 2012/0073086 A1* | 3/2012 | Rarick ................... B62K 21/26 16/436 |
| 2012/0123529 A1 | 5/2012 | Levi et al. |
| 2012/0239005 A1* | 9/2012 | Conway ............ A61M 25/0017 604/544 |
| 2012/0239142 A1 | 9/2012 | Liu et al. |
| 2013/0030519 A1 | 1/2013 | Tran et al. |
| 2013/0231641 A1* | 9/2013 | Gustavsson ......... A61M 25/002 604/544 |
| 2013/0317598 A1 | 11/2013 | Rowe et al. |
| 2014/0066905 A1* | 3/2014 | Young ................ A61M 25/002 604/544 |
| 2014/0296962 A1 | 10/2014 | Cartledge et al. |
| 2014/0364889 A1* | 12/2014 | Stubber .............. A61B 17/3415 606/185 |
| 2017/0065415 A1 | 3/2017 | Rupp et al. |
| 2018/0070927 A9* | 3/2018 | Hatta ............... A61B 17/00234 |
| 2018/0153689 A1 | 6/2018 | Maimon et al. |
| 2018/0344456 A1 | 12/2018 | Barash et al. |

FOREIGN PATENT DOCUMENTS

| | | |
|---|---|---|
| EP | 0592410 B1 | 10/1995 |
| EP | 0850607 A1 | 7/1998 |
| FR | 2815844 A1 | 5/2002 |
| NO | 2006138173 A2 | 12/2006 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 A1 | 6/2003 |
| WO | 2004019825 A1 | 3/2004 |
| WO | 2005084595 A1 | 9/2005 |
| WO | 2006032051 A2 | 3/2006 |
| WO | 2006111391 A1 | 10/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |

* cited by examiner

GRIPPING AND PUSHING DEVICE FOR MEDICAL INSTRUMENT

CROSS REFERENCE TO RELATED APPLICATIONS

This application is a continuation of U.S. patent application Ser. No. 16/222,992, filed Dec. 17, 2018, which in turn is a continuation of U.S. patent application Ser. No. 15/232,722, filed Aug. 9, 2016, now U.S. Pat. No. 10,179,046, which claims the benefit of U.S. Provisional Patent Application No. 62/205,567, filed Aug. 14, 2015. Each of these applications is expressly incorporated by reference herein.

FIELD

This invention relates generally to embodiments of a gripping and pushing device for inserting a medical instrument, such as a catheter, into a patient's body.

BACKGROUND

Elongated medical instruments are inserted into a patient's body to perform a wide variety of procedures. Catheters, for example, are often inserted into a subject to drain fluids, or used to deliver and implant a medical device, such as a stent or a prosthetic valve, at a location inside a subject. Cardiac catheterization, such as for performing angioplasty or implanting a prosthetic heart valve, can involve the use of a relatively long catheter that is advanced through a patient's vasculature to access the heart. In one approach, for example, the catheter can be advanced through a femoral artery and the aorta to access the heart.

Control and advancement of catheters, especially for cardiac catheterization, is difficult because of their construction. The user must frequently manipulate, or torque, the catheter shaft on the proximal end to facilitate advancement of the catheter with a desired orientation on the distal end. To provide the needed control over the movement of the catheter, it is necessary that these tubular catheters be made somewhat rigid. However, catheters must be flexible enough to navigate through the body lumen to arrive at the desired location within the body where the medical procedures will be performed. An overly rigid catheter shaft will not easily track, or follow, a guidewire. Because of their length, it is often necessary for the practitioner to grasp the relatively narrow shaft of the catheter at a location near the entry point into the patient's vasculature rather than the handle at the very proximal end of the catheter to avoid buckling of the shaft. Unfortunately, it is often difficult to obtain and maintain a sure grip on the relatively narrow shaft for the necessary control and grasping the shaft with a tight grip causes user fatigue.

Therefore, what has been needed is a device that improves a practitioner's ability to insert and control advancement of a medical instrument through a patient's body.

SUMMARY

The present disclosure is directed to embodiments of a gripping and pushing device for use with a medical instrument that is insertable into a patient's body. In particular embodiments, the gripping and pushing device is placed on a relatively narrow, elongated structure of the medical instrument, such as a shaft or tubular member. Instead of gripping the shaft directly, a practitioner can squeeze or grip the gripping and pushing device, which in turn grips the medical instrument and transfers pushing, pulling and/or rotational motion of the practitioner's hand to the shaft. The gripping and pushing device provides a larger gripping area for the practitioner to allow the practitioner to maintain a better grip and control over the medical instrument with less fatigue as the medical instrument is pushed into the patient's body, torqued, or otherwise manipulated within the patient's body.

To enhance the gripping force of the device against the shaft of the medical instrument, the device can include at least one gripping layer secured to an inner surface of a deflectable portion of the device. Gripping the deflectable portion causes the deflectable portion to deflect radially inwardly toward the shaft and press the gripping layer against the shaft. The gripping layer can be formed from a material having a greater coefficient of friction than the deflectable portion. In particular embodiments, the gripping layer is secured to the inner surface of the deflectable portion at axially spaced apart attachment locations (such as with a suitable adhesive) so as to define unsecured portions between the attachment locations. The unsecured portions of the gripping layer are axially deformable. Thus, when gripping and pushing forces are applied to the device, the unsecured portions can "bunch up" or form non-linear segments that further enhance the effective gripping force of the gripping layer against the shaft.

In one representative embodiment, a gripping and pushing device for a medical instrument comprises an elongated main body defining a lumen. The elongated main body comprises one or more deflectable portions that can be pressed radially inwardly toward a shaft of the medical instrument extending through the lumen. One or more elastomeric gripping layers can be secured to the inner surface of a respective deflectable portion at axially spaced apart attachment locations. The one or more gripping layers are axially deformable relative to the one or more deflectable portions between the attachment locations when manual pressure is applied to the one or more deflectable portions to press the one or more gripping layers against the shaft and move the shaft longitudinally into a patient's body.

In another representative embodiment, a method of inserting a medical instrument into the body of a patient comprises gripping a gripping and pushing device disposed on a shaft of the medical instrument. The gripping and pushing device comprises at least one elongated deflectable portion and at least one gripping layer secured to an inner surface of the deflectable portion at axially spaced attachment locations, wherein gripping the gripping and pushing device causes the deflectable portion to deflect toward the shaft and press the gripping layer against the shaft. While gripping the gripping and pushing device, the gripping and pushing device is pushed toward the patient to advance the medical instrument into the patient's body.

In another representative embodiment, a medical assembly comprises a delivery apparatus for delivering a prosthetic device into a patient's body. The delivery apparatus comprises a handle and an elongated shaft extending from the handle. The assembly further comprises a gripping and pushing device disposed on the shaft of the delivery apparatus. The gripping and pushing device comprises an elongated main body defining a lumen through which the shaft extends. The elongated main body comprises at least one deflectable portion and at least one gripping layer secured to an inner surface of the deflectable portion at axially spaced apart attachment locations so as to define one or more unsecured portions of the gripping layers between the attachment locations. The deflectable portion is deflectable from a non-deflected position with the gripping layer radially spaced from the shaft and a deflected position with the gripping layer engaging the shaft.

The foregoing and other objects, features, and advantages of the invention will become more apparent from the following detailed description, which proceeds with reference to the accompanying figures.

DETAILED DESCRIPTION

For purposes of this description, certain aspects, advantages, and novel features of the embodiments of this disclosure are described herein. The present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present, or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

The present disclosure is directed to embodiments of a gripping and pushing device for use with a medical instrument that is insertable into a patient's body. The illustrated embodiment is described in the context of inserting a delivery apparatus or catheter into a patient's vasculature. However, it should be understood that the embodiments disclosed herein can be used with any of various medical instruments to perform any of various medical procedures, such as administration of medication or fluids, implantation of prosthetic devices, drainage of fluids, to name a few examples. Some examples of medical instruments (other than catheters) that can be used with the disclosed embodiments include but are not limited to, needles, stylets, cannulas, endoscopic devices, laparoscopic instruments, and/or combinations thereof.

In general, the gripping and pushing device is placed on a relatively narrow, elongated structure of the medical instrument, such as a shaft or tubular member. Instead of gripping the shaft directly, a practitioner can squeeze or grip the gripping and pushing device, which in turn grips the medical instrument and transfers pushing, pulling and/or rotational motion of the practitioner's hand to the shaft. The gripping and pushing device provides a larger gripping area for the practitioner to allow the practitioner to maintain a better grip and control over the medical instrument with less fatigue. This can be especially helpful when the practitioner is wearing gloves made from latex or other polymers, the outer surface of which can become slippery if covered in blood, saline, or other fluid.

Figures 1, 2, 3:
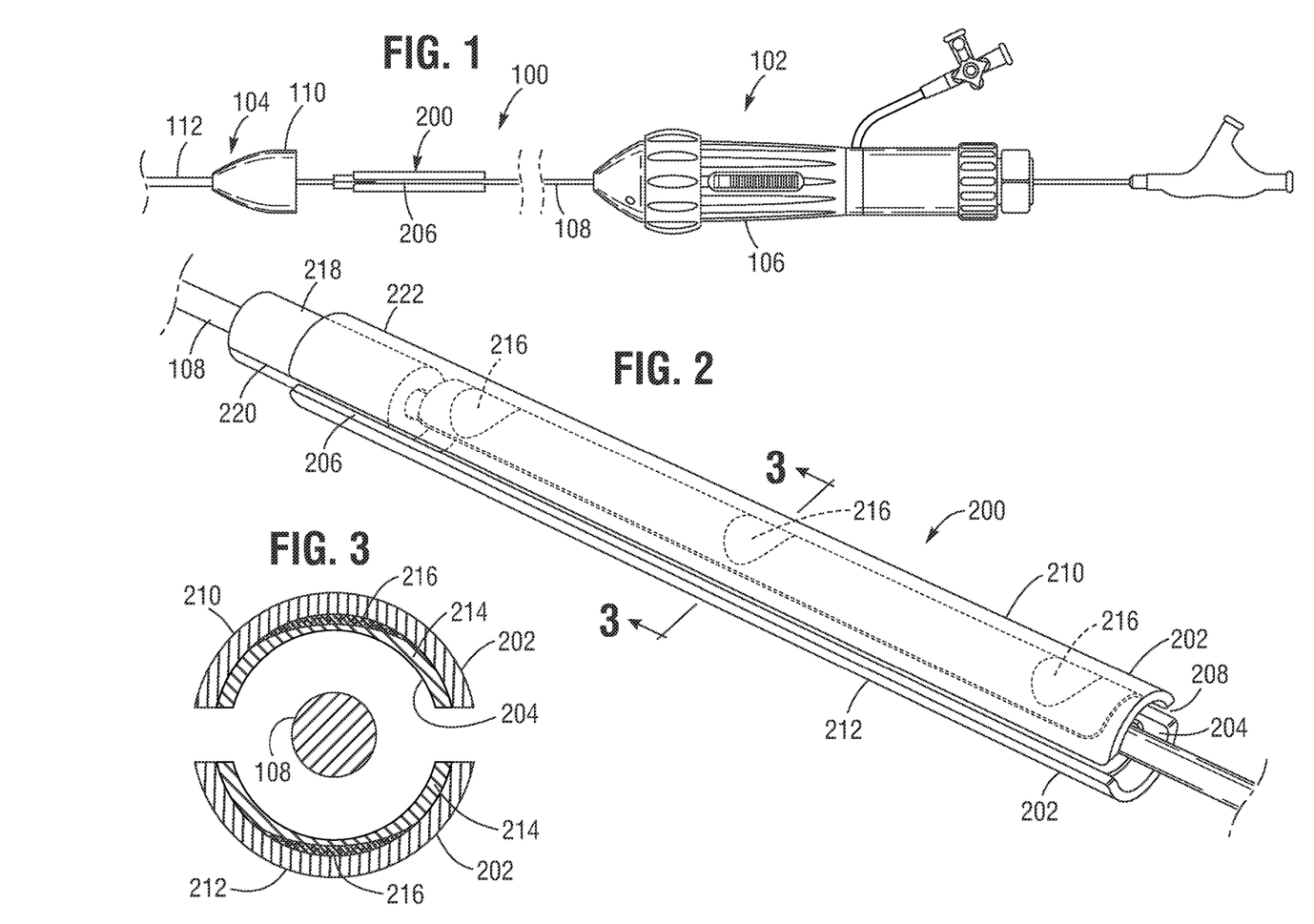
FIG. 1 is a side elevation view of a delivery system for delivering a prosthetic device into a patient's body, showing a catheter gripping and pushing device disposed on a shaft of a delivery catheter of the system.
FIG. 2 is a perspective view of the catheter gripping and pushing device of FIG. 1.
FIG. 3 is a cross-sectional view of the catheter gripping and pushing device taken along line 3-3 of FIG. 2.

FIG. 1 shows a delivery system 100 for a delivering a prosthetic device (e.g., a prosthetic valve or stent) into the body of a patient. The delivery system 100 can include a delivery apparatus (also referred to as a delivery catheter) 102 and an introducer 104. The delivery apparatus 102 can include a handle 106 and an elongated shaft 108 extending distally from the handle 106. An implantable prosthetic device (e.g., a prosthetic valve or stent) (not shown) can be mounted in a compressed state on a distal end portion of the shaft 108 for delivery into the patient's body.

The shaft 108 can be sized and shaped to be advanced through the patient's vasculature to a desired implantation site for the prosthetic device. For example, for delivering a prosthetic heart valve in a transfemoral procedure, the shaft 108 is pushed through a femoral artery and the aorta in a retrograde direction to access the heart. In another transfemoral procedure, the shaft 108 is pushed through a femoral vein and the inferior vena cava in an antegrade direction to access the heart. For transfemoral delivery of a prosthetic valve to the heart, the shaft 108 can have a length of 48 inches or longer.

The introducer 104 can include a housing 110 and an elongated sheath 112 extending distally from the housing 110. In use, the sheath 112 can be inserted first into the access location of the patient's vasculature (e.g., a surgical cut down of a femoral artery) and the shaft 108 of the delivery apparatus 102 can then be inserted through the introducer 104 and into the patient's vasculature. The housing 110 can have one or more seals (not shown) that can engage the shaft 108 and therefore minimize blood loss during the procedure. The introducer 104 facilitates the initial introduction of the delivery apparatus into the vasculature and can protect against trauma to the vessel where the delivery apparatus is inserted. In some applications, however, the delivery apparatus 102 may be inserted directly into the patient's vasculature without the use of the introducer 104. Further details of the delivery apparatus 102 and the introducer 104 are described in U.S. Patent Application Publication 2013/0030519, which is incorporated herein by reference.

As further shown in FIG. 1, a catheter gripping and pushing device 200, according to one embodiment, is mounted on the shaft 108 of the delivery apparatus 102 and can be used for manipulating the shaft 108, such as for pushing the shaft into the patient's vasculature (e.g., a femoral artery and the aorta) and/or torqueing the shaft to effect steering or placement of the prosthetic device within the body. It should be understood that the gripping and pushing device 200 could be used in a variety of other applications for pushing and/or manipulating catheters and other medical instruments within various parts of the body and is not limited for use with a delivery apparatus for delivering a prosthetic device.

Figure 5A:
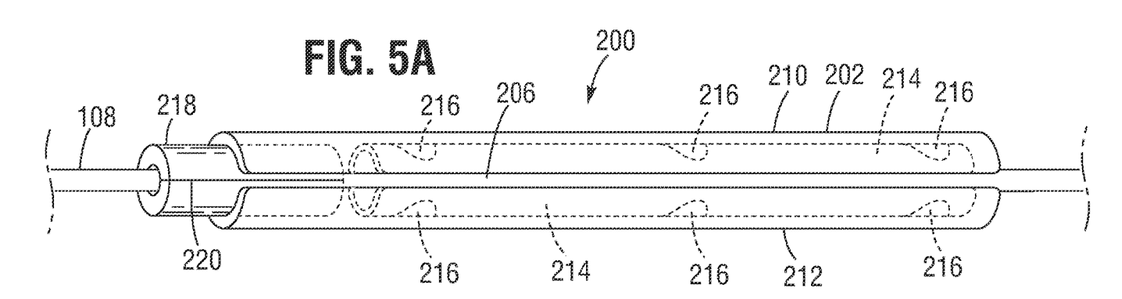
FIG. 5A is a side elevation view of the catheter gripping and pushing device of FIG. 1 shown in a relaxed, non-use position.
Figure 6:
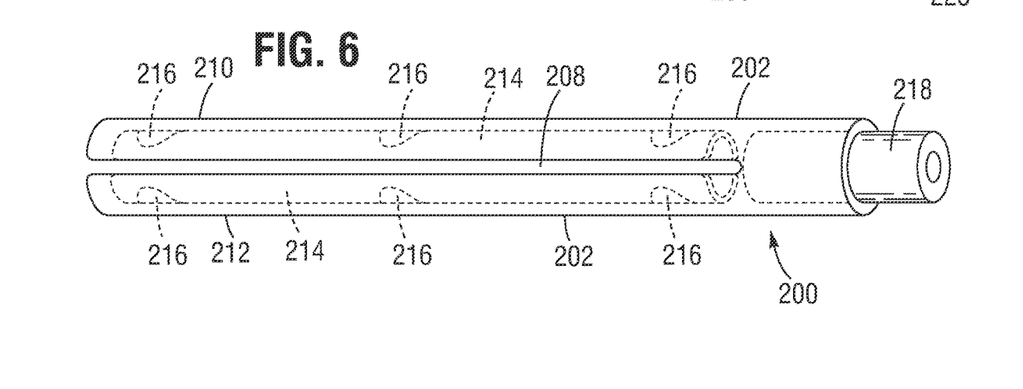
FIG. 6 is a side elevation view of the catheter gripping and pushing device of FIG. 1, showing the opposite side the device from the view shown in FIG. 5B.

As best shown in FIGS. 2 and 3, the pushing device 200 in the illustrated embodiment comprises an elongated main body 202 mounted on and extending from an inner tube or shaft 218. The body 202 defines a lumen 204 and can be formed with first and second longitudinally extending slots 206, 208, respectively on opposite sides of the body, thereby defining two elongated, deflectable portions, such as in the form of diametrically opposed legs 210, 212. The first slot 206 can extend the entire length of the body 202 (FIG. 5A), while the second slot 208 can be a partial slot extending less than the entire length of the body 202. For example, the second slot 208 can extend from the proximal end of the body 202 to a location at the proximal end of the inner tube 218 (FIG. 6). A distal end portion 222 of the body 202 is secured to the inner tube 218 (e.g., with a suitable adhesive) such that the legs 210, 212 are cantilevered from the inner tube 218 and can be pressed inwardly toward each other and against the shaft during use, as further described below.

Although in the illustrated embodiment the pushing device includes two slots 206, 208 and two legs 210, 212, the pushing device can be formed with any number of slots and legs in alternative embodiments. In other embodiments, the body 202 need not be formed with separate legs 210, 212 but is otherwise deformable or deflectable to allow opposing portions of the body 202 to be pressed against the shaft 108 during use. In one implementation, for example, the main body can have a substantially C-shaped cross-section (in a plane perpendicular to the length of the main body) defining one slot extending partially or along the entire length of the main body, wherein opposing sides of the main body are deflectable and can be pressed against the shaft 108 during use. In another implementation, the main body can have a substantially circular cross-section without any slots (or another closed annular shape) and is sufficiently flexible to allow opposing sides of the main body to be pressed inwardly against the shaft 108.

The inner tube 218 can be formed with a longitudinal slit 220 that is aligned with the first slot 206. In this manner, the pushing device 200 can be placed on the shaft 108 from the side by pushing the shaft 108 laterally through the first slot 206 and the slit 220 such that the shaft 108 extends co-axially through the inner tube 218 and the lumen 204 of the body. Conversely, the pushing device 200 can be removed the shaft 108 by simply by pulling the pushing device 200 laterally away from the shaft 108 so that the shaft 108 slides through the slit 220 and the first slot 206. In other embodiments, the inner tube 218 need not be formed with a slit 220, in which case the pushing device 200 would be placed on the shaft 108 by threading an end of the shaft co-axially through the inner tube 218.

Figure 4A:
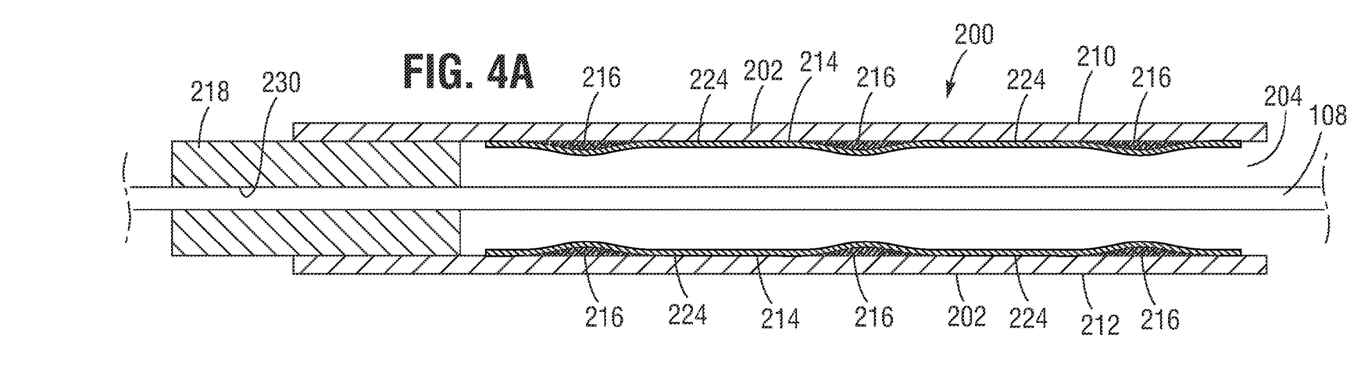
FIG. 4A is a cross-sectional view of the catheter gripping and pushing device of FIG. 1 taken along a plane extending lengthwise of the gripping and pushing device, showing the gripping and pushing device in a relaxed, non-use position.
Figure 4B:
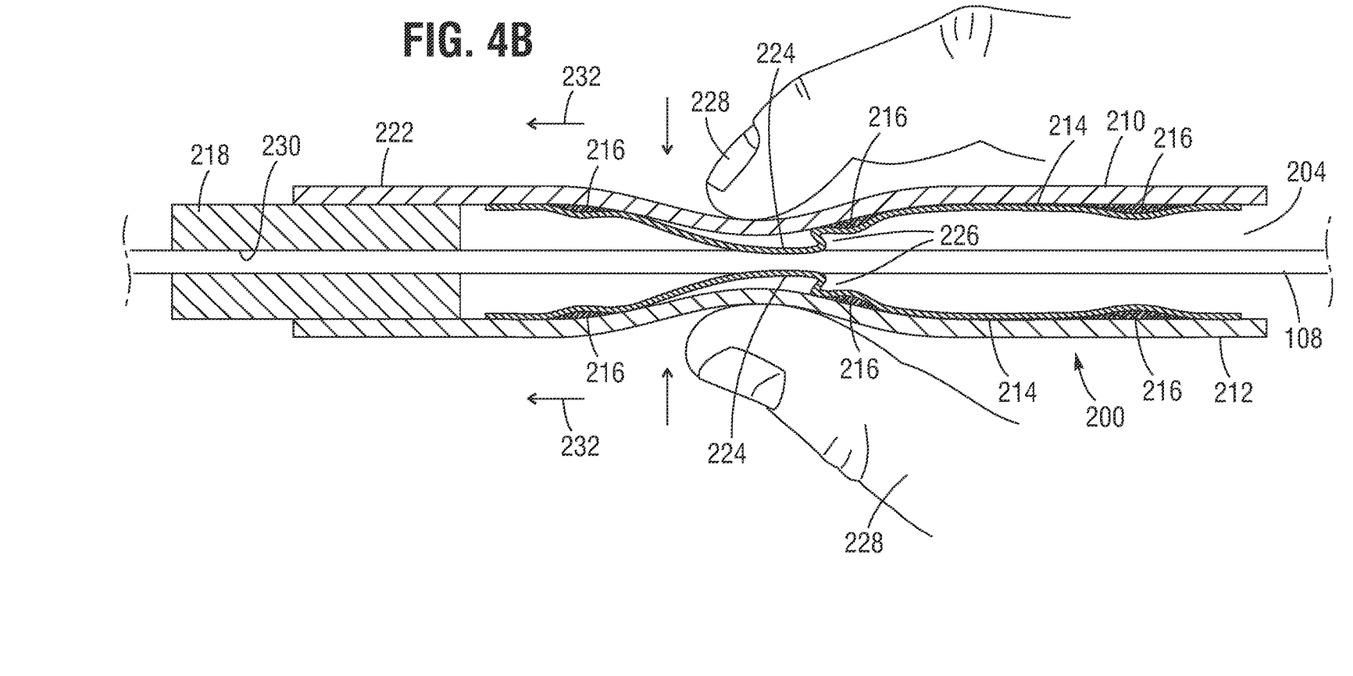
FIG. 4B is a cross-sectional view of the catheter gripping and pushing device similar to FIG. 4A but showing the gripping and pushing device being used to grip and push the shaft of the delivery catheter into the patient's body.

Secured to the inner surface of each leg 210, 212 is an inner gripping layer, or gripping strip, 214. As best shown in FIG. 4A, each gripping layer 214 can be secured to a respective leg 210, 212 by one or more axially spaced-apart attachment locations, such as the illustrated adhesive spots 216, defining unsecured portions 224 of the layers 214 between the attachment locations that are unattached to the inner surfaces of the legs 210, 212. The unsecured portions 224 can deform under manual pressure of user pressing against the legs 210, 212 to enhance the gripping action of the layers 214, as further described below. The thickness of the adhesive spots 216 shown in FIGS. 4A and 4B are exaggerated for purposes of illustration. In lieu of or in addition to the use of an adhesive, other techniques and/or mechanisms can be used to secure the gripping layers 214 to the legs 210, 212 at spaced-apart attachment locations, such as but not limited to, thermal welding, mechanical fasteners, and/or combinations thereof.

As best shown in FIG. 2, each gripper layer 214 in the illustrated embodiment is secured to a respective leg 210, 212 at three spaced-apart attachment locations by three spaced-apart adhesive spots 216. In alternative embodiments, each gripping layer 214 can be secured to a respective leg 210, 212 at greater than or fewer than three attachment locations. The adhesive spots 216 are separate layers of an adhesive disposed between the inner surface of the legs 210, 212 and the outer surface of the gripping layers 214 and can have any of various shapes (e.g., circular, elliptical, etc.). The adhesive spots 216 can be equally spaced from each other as shown in the drawings. Alternatively, the spacing between adjacent adhesive spots 216 can vary along the length the pushing device. Also, the spacing and/or positioning of the adhesive spots 216 of one gripping layer 214 can be different than the spacing and/or positioning of the adhesive spots of another gripping layer 214. In other embodiments, additional gripping layers 214 can be secured to each other at spaced apart attachment locations. For example, multiple gripping layers can be secured to the inner surface of one or both legs 210, 212 with adjacent gripping layers being secured to each other at spaced apart attachment locations.

Figure 5B:
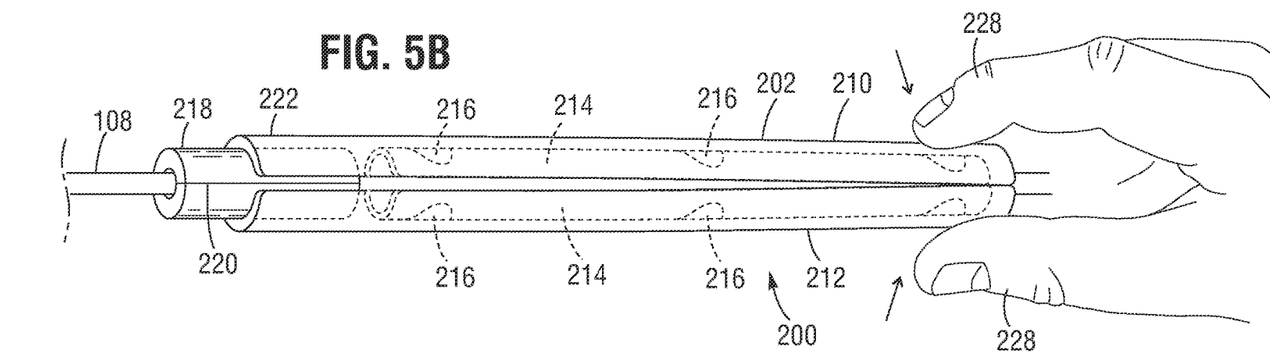
FIG. 5B is a side elevation view of the catheter gripping and pushing device of FIG. 1 shown being used to grip the shaft of the delivery catheter.

Referring to FIGS. 4A and 4B, the inner tube 218 has a lumen 230 sized and shaped to receive the shaft 108. The diameter of the lumen 230 can be slightly greater than the diameter of the shaft 108 to allow the pushing device 200 to slide along the length of the shaft 108. The lumen 204 of the body 202 is oversized relative to the shaft 108, which allows the legs 210, 212 to move between a non-deflected state in which the legs are spaced apart from the shaft 108 (FIGS. 4A and 5A) and a deflected state in which the legs are pressed against the shaft 108 by manual pressure from a user's hand (FIGS. 4B and 5B).

The body 202 desirably comprises a material with sufficient flexibility and/or elasticity to be easily compressed under manual pressure allowing the internal gripping layers 214 to contact the shaft 108 when gripping pressure is applied and revert back to the non-deflected state under its own resiliency when gripping pressure is released. Any of various suitable materials, such as any of various metals (e.g., stainless steel) or polymeric materials can be used to form the body 202, such as but not limited to Nylon, Pebax, and/or combinations thereof. The legs 210, 212 can have roughened or textured inner and outer surfaces to enhance adherence with the gripping layers 214 and improve gripping by a user's hand. The inner gripping layers 214 desirably comprise an elastomeric material that can deform when manual pressure is applied to the legs 210, 212. In some embodiments, the gripping layers 214 are formed from a material that is relatively more elastic and/or deformable than the legs 210, 212 and has a relatively greater coefficient of friction with respect to the shaft 108 than the legs and a relatively low shore A hardness. Any of various suitable elastomers can be used for forming the gripping layers 214 such as, for example, low hardness silicone rubber.

The inner tube 218 can be made from any of various suitable materials, such as any of various polymeric materials, such as but not limited to Nylon, Pebax, PTFE, and/or combinations thereof. In some embodiments, the inner tube 218 can be made from a low-friction material and can have a relatively low coefficient of friction with respect to the shaft 108 compared to the gripping layers 214 to promote sliding of the pushing device 200 relative to the shaft when the legs 210, 212 are not in contact with the shaft. In some embodiments, the inner tube 218 can include an inner liner or layer of low friction material, such as PTFE, to reduce sliding friction with the shaft 108.

In some embodiments, the outer surface of the body 202 can be provided with gripping layers (not shown) similar to gripping layers 214 to enhance a user's grip on the body 202. For example, elongated gripping layers can be placed along the outer surface of the legs 210, 212 in alignment with the gripping layers 214. The gripping layers on the outer surface of the body can be formed from the same materials as the gripping layers 214 (e.g., silicone rubber).

In use, the pushing device 200 is placed on the shaft 108 of the delivery apparatus 102 as shown in FIG. 1. In many applications, such as in procedures for implanting prosthetic heart valves, the shaft 108 can be several feet long and is relatively flexible. Consequently, the physician may need to grasp the shaft 108 close to the insertion point of the patient's body and away from the handle 106 while pushing the shaft into the body to prevent buckling of the shaft. Thus, the pushing device 200 can be initially positioned along the shaft 108 at a desired distance from the entry point and the introducer 104 (if used), such as a few inches from the entry point.

The legs 210, 212 of the pushing device 200 can then be squeezed between the fingers 228 (e.g., a thumb and an index finger) to press the gripping layers 214 against the shaft 108. While maintaining manual pressure against the legs 210, 212, the pushing device 200 is advanced distally in the direction of arrows 232, which pushes the shaft 108 through the introducer 104 and into the patient's vasculature. As illustrated in FIG. 4B, the unsecured portions 224 of the gripping layers 214 between the adhesive spots 216 are axially deformable, and can bunch up and/or or stretch or deform axially, forming wave-like deformations that enhance the gripping force against the shaft 108 and minimize slippage of the gripping device relative to the shaft. Thus, the deformation of the gripping layers 214 allow the physician to push the shaft 108 through the patient's vasculature with less manual force, thereby reducing finger fatigue and enhancing control over the shaft 108.

After the pushing device 200 has been moved distally to a location at the introducer 104 (which is effective to insert the shaft 108 partially into the patient's vasculature), manual pressure can be released from the legs 210, 212 (which can revert back to their non-deflected state), and the pushing device 200 can be slid proximally relative to the shaft 108 and away from the patient a desired distance, such as by grasping the inner tube 218 or the distal end portion 222 of the body and retracting the pushing device relative to the shaft. Thereafter, the physician can again grasp the legs 210, 212 and use the pushing device 200 to push the shaft 108 further into the patient's vasculature. The process of retracting the pushing device and using the pushing device to push the shaft further into the patient's body can be repeated as needed until the handle 106 can be effectively used to push or otherwise manipulate the shaft without buckling.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A gripping and pushing device for a medical instrument comprising:
    an elongated body defining a lumen, the elongated body comprising a plurality of deflectable portions that can be deflected radially inwardly towards a longitudinal axis extending through the lumen, each of the plurality of deflectable portions having an inner surface; and
    one or more gripping layers, each secured to the inner surface of a respective deflectable portion of the plurality of deflectable portions, wherein the one or more gripping layers are deformable along the longitudinal axis;
    wherein the plurality of deflectable portions move radially inward toward the longitudinal axis when manual pressure is applied to the plurality of deflectable portions.

2. The gripping and pushing device of claim 1, in combination with the medical instrument, the medical instrument comprising a shaft, the shaft being disposed within the lumen.

3. The gripping and pushing device of claim 1, wherein the plurality of deflectable portions comprise first and second deflectable portions formed as first and second diametrically opposed leg portions, and the one or more gripping layers of the first and second leg portions comprise first and second diametrically opposed gripping layers secured to the first and second leg portions, respectively.

4. The gripping and pushing device of claim 1, wherein each of the one or more gripping layers is secured to the inner surface of a respective deflectable portion at a plurality of spaced apart locations and is not secured to the inner surface between the spaced apart locations.

5. The gripping and pushing device of claim 1, wherein the device is split longitudinally along its entire length to permit placement of a shaft of the medical instrument within the lumen laterally from one side of the device.

6. The gripping and pushing device of claim 1, wherein the device comprises a plurality of longitudinal slits that extend along the entire length of the lumen.

7. A gripping and pushing device for a medical instrument comprising:
- an inner tube defining a first lumen;
- an elongated main body extending from the inner tube and defining a second lumen, the second lumen being in communication with, and coaxial to, the first lumen, the elongated main body comprising one or more deflectable portions that can be pressed radially inwardly towards a longitudinal axis extending through the second lumen, each deflectable portion having an inner surface; and
- one or more gripping layers, each secured to the inner surface of a respective deflectable portion.

8. The gripping and pushing device of claim 7, wherein the inner tube is made of a material that is more rigid than a material from which the elongated main body is made.

9. The gripping and pushing device of claim 7, wherein the inner tube is configured to maintain engagement with a shaft of the medical instrument inserted through the first lumen and the one or more deflectable portions are configured to selectively engage a portion of the shaft extending through the second lumen.

10. The gripping and pushing device of claim 7, wherein the device is split longitudinally along its entire length to permit placement of a shaft of the medical instrument laterally within the first and second lumens from one side of the device.

11. The gripping and pushing device of claim 7, wherein the device comprises a plurality of longitudinal slits formed in a radial outer surface of the inner tube and a radial outer surface of the main body, wherein a shaft of the medical instrument can be placed within the first and second lumens by inserting the shaft through a lateral slit of the plurality of lateral slits.

12. The gripping and pushing device of claim 7, wherein each of the one or more gripping layers is secured to the inner surface of a respective deflectable portion at a plurality of spaced apart locations and is not secured to the inner surface between the spaced apart locations.

13. The gripping and pushing device of claim 7, wherein the one or more gripping layers are deformable along the longitudinal axis.

14. A gripping and pushing device for a medical instrument comprising:
- an inner tube defining a first lumen; and
- an elongated main body extending from the inner tube and defining a second lumen, the second lumen being in communication with, and coaxial to, the first lumen, the elongated main body comprising a plurality of circumferentially spaced-apart deflectable portions, wherein each of the plurality of deflectable portions comprise a gripping surface and can be pressed radially inwardly towards a longitudinal axis extending through the second lumen.

15. The gripping and pushing device of claim 14, wherein the device is split longitudinally along its entire length to permit placement of a shaft of the medical instrument within the first and second lumens laterally from one side of the device.

16. The gripping and pushing device of claim 14, wherein the device comprises a plurality of longitudinal slits formed in a radial outer surface of the inner tube and a radial outer surface of the main body, wherein a shaft of the medical instrument can be placed within the first and second lumens by inserting the shaft through a lateral slit of the plurality of lateral slits.

17. The gripping and pushing device of claim 14, wherein the gripping surface of at least one deflectable portion of the plurality of deflectable portion comprises one or more gripping layers secured to the inner surface of the at least one respective deflectable portion.

18. The gripping and pushing device of claim 17, wherein the one or more gripping layers of a respective deflectable portion of the plurality of deflectable portions are secured to the inner surface of the respective deflectable portion at a plurality of spaced apart locations, wherein between spaced apart locations of the plurality of spaced apart locations at least one gripping layer of the one or more gripping layers are not secured to the inner surface.

19. The gripping and pushing device of claim 17, wherein the one or more gripping layers are deformable along the longitudinal axis.

20. A gripping and pushing device for a medical instrument comprising:
- an elongated body defining a lumen, the elongated body comprising a plurality of deflectable portions that can be deflected radially inwardly towards a longitudinal axis extending through the lumen, each of the plurality of deflectable portions having an inner surface; and
- one or more gripping layers, each secured to the inner surface of a respective deflectable portion of the plurality of deflectable portions;
- wherein the plurality of deflectable portions move radially inward toward the longitudinal axis when manual pressure is applied to the plurality of deflectable portions and wherein the device is split longitudinally along its entire length to permit placement of a shaft of the medical instrument within the lumen laterally from one side of the device.

21. The gripping and pushing device of claim 20, in combination with the medical instrument, the medical instrument comprising a shaft, the shaft being disposed within the lumen.

22. The gripping and pushing device of claim 20, wherein the plurality of deflectable portions comprise first and second deflectable portions formed as first and second diametrically opposed leg portions, and the one or more gripping layers of the first and second leg portions comprise first and second diametrically opposed gripping layers secured to the first and second leg portions, respectively.

23. The gripping and pushing device of claim 20, wherein each of the one or more gripping layers is secured to the inner surface of a respective deflectable portion at a plurality of spaced apart locations and is not secured to the inner surface between the spaced apart locations.

24. The gripping and pushing device of claim 20, wherein the device comprises a plurality of longitudinal slits that extend along the entire length of the lumen.

* * * * *